United States Patent [19]
Oehrli et al.

[11] 4,075,229
[45] Feb. 21, 1978

[54] PROCESS FOR STABILIZING METALDEHYDE AND STABILIZED COMPOSITION

[75] Inventors: Beat Oehrli, Visp; Max Mettler, Ried near Brig; Bruno Righetti, Naters, all of Switzerland

[73] Assignee: Lonza, Ltd., Gampel, Switzerland

[21] Appl. No.: 706,272

[22] Filed: July 19, 1976

[30] Foreign Application Priority Data

July 18, 1975 Switzerland .................... 009416/75

[51] Int. Cl.$^2$ ........................................... C07D 323/04
[52] U.S. Cl. .................................................. 260/340
[58] Field of Search ......................................... 260/340

[56] References Cited

U.S. PATENT DOCUMENTS

| | | | |
|---|---|---|---|
| 1,612,032 | 12/1926 | Lichtenhahn et al. | 260/340 |
| 1,631,875 | 6/1927 | Luscher | 260/340 |
| 1,763,326 | 6/1930 | Reed | 260/340 |
| 2,230,591 | 2/1941 | Fischer et al. | 260/601 |
| 3,403,168 | 9/1968 | Zima | 260/340 |

*Primary Examiner*—Norma S. Milestone
*Attorney, Agent, or Firm*—Virgil H. Marsh

[57] ABSTRACT

Process for stabilizing metaldehyde which involves mixing the metaldehyde and 0.005 to 5 percent by weight, based on the weight of the metaldehyde, of an inorganic base or organic base having a pK number of 6.5 to 12.5. The inorganic base or the organic base stabilizes the metaldehyde.

Stabilized metaldehyde which contains metaldehyde and 0.005 to 5 percent by weight, based on the weight of the metaldehyde, of an inorganic base or an organic base having a pK number of 6.5 to 12.5. The inorganic base or the organic base stabilizes the metaldehyde.

4 Claims, No Drawings

PROCESS FOR STABILIZING METALDEHYDE AND STABILIZED COMPOSITION

BACKGROUND OF THIS INVENTION

1. Field of This Invention

This invention relates to stabilizing metaldehyde and the resultant stabilized metaldehyde.

2. Prior Art

Metaldehyde, prepared from acetaldehyde by the action of acids or haloid salts, is a white solid having the formula $(C_2H_4O)_4$, i.e., a tetramer of acetaldehyde. If the metaldehyde is not freed by recrystallization of the last traces of catalyst, there is a tendency on the part of the metaldehyde to decomposition even at ambient temperature and particularly at high temperature; the metaldehyde fluidizes to paraldehyde. By treatment with reagents that render the catalysts harmless (such reagents being, for example, barium or silver compounds, paraformaldehyde and weak bases, such as, ammonia or ammonium carbonate), the tendency of the metaldehyde to decomposition can be diminished—but such effect is not stable or has other disadvantages, such as, the appearance of ash of the metaldehyde stabilized by salts in combustion. In addition, drying of metaldehyde so far could only be effected at temperatures of at most about 30° C.

BROAD STATEMENT OF THIS INVENTION

An object of this invention is to provide an economical process for stabilizing metaldehyde that overcomes the disadvantages of the known stabilizing processes and that affords much higher stabilization. Another object of this invention is to provide stabilized metaldehyde that is much more highly stabilized than previously.

Other objects and advantages of this invention are set out herein or are obvious herefrom to one ordinarily skilled in the art.

The objects and advantages of this invention are achieved by the process and product of this invention.

This invention is addressed to the problems of overcoming the disadvantages of the known stabilizing processes and of producing a new economical process that affords a significantly higher stability for the metaldehyde. Such is achieved by this invention in that there is mixed into the metaldehyde 0.005 to 5 percent by weight, advantageously 0.05 to 1 percent by weight, based on the weight of the metaldehyde, of an inorganic base or an organic base having a pK number of at least 6.5, or 7.5, to 12.5.

This invention includes stabilized metaldehyde which contains metaldehyde and 0.005 to 5 percent by weight, based on the weight of the metaldehyde, of an inorganic base or an organic base having a pK number of 6.5 to 12.5. The inorganic base or organic base stabilizes the metaldehyde.

With the method of stabilization of this invention, the stability of metaldehyde even at temperatures of 60° C. is greatly improved.

DETAILED STATEMENT OF THIS INVENTION

Preferably the stabilizers have a pK of 7.5 to 12.5. pK is the dissociation constant of the stabilizer in an aqueous solution.

The stabilizer can be an alkyl pyridine having the formula:

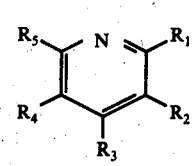

wherein $R_1$, $R_2$, $R_3$, $R_4$ and $R_5$ are each hydrogen or an alkyl group having 1 to 5 carbon atoms, preferably 1 to 3 carbon atoms. $R_1$, $R_2$, $R_3$, $R_4$ and/or $R_5$ can be the same or different alkyl groups. Preferably one or two of $R_1$, $R_2$, $R_3$, $R_4$, and $R_5$ are alkyl groups. Examples of alkyl pyridines which are useful stabilizers of metaldehyde are pyridine, 2-methyl pyridine, 4-methyl pyridine, 2,6-dimethylpyridine and 2-methyl-5-ethyl-pyridine.

Other useful stabilizers are quinoline and pyrazole, both of which are advantageous.

The most preferred stabilizer is nicotinic acid amide, which is:

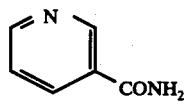

The most preferred group of stabilizers are pyridine-3-carboxylic acid derivative (i.e., nicotinic acid derivatives), of which a highly preferred group are the alkyl esters and aryl esters of nicotinic acid, that are:

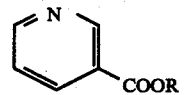

wherein R can be an alkyl group havin 1 to 5 carbon atoms, preferably 1 to 3 carbon atoms, or an aryl group such as $-C_6H_5$ or $-CH_2C_6H_5$. Examples of such stabilizers are nicotinic acid methyl ester, nicotinic acid ethyl ester and nicotinic acid benzyl ester.

Examples of inorganic bases having pH of 6.5 to 12.5 that are useful stabilizers are: beryllium hydroxide (pK = 10.3) and hydroxylamine (pK = 7.97).

Mixtures of stabilizers can be used.

The mixing in of the solid stabilizer can be achieved in pulverized form or in solution form (for example, nicotinic acid amide as a 30 percent aqueous solution) directly in the dryer, where the metaldehyde, which is centrifuged off, is dried. The liquid stabilizers are also easy to meter into th dryer.

This invention also includes stabilized metaldehyde which consists essentially of metaldehyde and 0.005 to 5 percent by weight, based on the weight of the metaldehyde, of at least one inorganic base and/or organic base having a pK number of 6.5 to 12.5. The inorganic base or organic base stabilizes the metaldehyde.

This invention further includes stabilized metaldehyde which consists essentially of metaldehyde and 0.005 to 5 percent by weight, based on the weight of the metaldehyde, of at least one inorganic base and/or organic base having a pK number of 6.5 to 12.5. The inorganic base or organic base stabilizes the metaldehyde.

The following examples illustrate the process of the invention.

EXAMPLES 1 TO 17

In each example, the quality of the stabilized metaldehyde was tested by storing 20 gm. of metaldehyde with a specific amount of stabilizer in a 250 ml powder flask (open) at 60° C. After 4 days the decrease in weight in each instance was determined. The test results are given in the table.

Examples 1 to 11, which represents this invention, had far less weight losses than did unstabilized metaldehyde (Example 12) or metaldehyde stabilized with prior art stabilizers (Examples 13 to 17).

TABLE

| Example No | Stabilizer | Amount of stabilizer weight percent | Weight Loss After 4 days weight percent | pK Number of stabilizer |
|---|---|---|---|---|
| 1 | pyridine | 1 | 6.2 | 8.77 |
| 2 | 2-methylpyridine | 1 | 4.2 | 7.52 |
| 3 | 4-methylpyridine | 1 | 4.3 | 8.00 |
| 4 | 2,6-dimethylpyridine | 0.5 | 2.5 | >6.50 |
| 5 | 2-methyl-5-ethylpyridine | 1 | 1.3 | >6.50 |
| 6 | quinoline | 1 | 1.6 | 9.20 |
| 7 | pyrazole | 0.5 | 2.4 | 11.52 |
| 8 | nicotinic acid-methyl ester | 0.5 | 1.7 | >6.50 |
| 9 | nicotinic acid-ethyl ester | 0.5 | 1.2 | >6.50 |
| 10 | nicotinic acid benzyl ester | 0.5 | 1.6 | >6.50 |
| 11 | nicotinic acid amide | 0.5 | 1.0 | >6.50 |
| 12 | without any stabilizer | — | 48.5 | — |
| 13 | ammonia | 1 | 10.1 | ≈4.8 |
| 14 | ammonia carbonate | 1 | 8.3 | — |
| 15 | soda | 1 | 40.9 | — |
| 16 | triethyl amine | 1 | 47.4 | 3.24 |
| 17 | paraformaldehyde | 1 | 29.7 | — |

What is claimed is:

1. A process for stabilizing metaldehyde, which comprises mixing said metaldehyde and 0.005 to 5 percent by weight, based on the weight of said metaldehyde, of nicotinic acid amide, stabilizing said metaldehyde.

2. A process as claimed in claim 1 wherein 0.05 to 1 percent by weight, based on the weight of said metaldehyde, of said nicotinic acid amide is used.

3. Stabilized metaldehyde which comprises metaldehyde and 0.005 to 5 percent by weight, based on the weight of said metaldehyde, of nicotinic acid amide, said nicotinic acid amide stabilizing said metaldehyde.

4. Stabilized metaldehyde as claimed in claim 3 wherein 0.05 to 1 percent by weight, based on the weight of said metaldehyde, of said nicotinic acid amide is used.

* * * * *